US011129558B2

(12) United States Patent
Washington (10) Patent No.: US 11,129,558 B2
(45) Date of Patent: Sep. 28, 2021

(54) URINARY COLLECTION SYSTEM AND PROCEDURE FOR DECREASING CATHETER-ASSOCIATED BACTERIURIA

(71) Applicant: Eric A. Washington, Gary, IN (US)

(72) Inventor: Eric A. Washington, Gary, IN (US)

(*) Notice: Subject to any disclaimer, the term of this patent is extended or adjusted under 35 U.S.C. 154(b) by 445 days.

(21) Appl. No.: 15/268,571

(22) Filed: Sep. 17, 2016

(65) Prior Publication Data

US 2017/0079571 A1 Mar. 23, 2017

Related U.S. Application Data

(60) Provisional application No. 62/220,316, filed on Sep. 18, 2015.

(51) Int. Cl.
| | | |
|---|---|---|
| *A61B 5/20* | (2006.01) | |
| *A61B 10/00* | (2006.01) | |
| *A61F 5/44* | (2006.01) | |
| *A61F 5/441* | (2006.01) | |
| *A61F 5/442* | (2006.01) | |

(Continued)

(52) U.S. Cl.
CPC .......... *A61B 5/207* (2013.01); *A61B 5/14507* (2013.01); *A61B 5/14532* (2013.01); *A61B 5/14539* (2013.01); *A61B 5/14546* (2013.01); *A61B 5/6828* (2013.01); *A61B 10/007* (2013.01); *A61F 5/441* (2013.01);
(Continued)

(58) Field of Classification Search
None
See application file for complete search history.

(56) References Cited

U.S. PATENT DOCUMENTS 3,312,221 A  4/1967 Overment
4,233,263 A  11/1980 Schaeffer
(Continued)

FOREIGN PATENT DOCUMENTS

EP  0 145 505 A2  6/1985
GB  2080116 A * 2/1982 ............... A61F 5/44
(Continued)

OTHER PUBLICATIONS

International Search Report, dated Jan. 3, 2017, for PCT/US16/52388.
(Continued)

*Primary Examiner* — Matthew Kremer
(74) *Attorney, Agent, or Firm* — Hartman Global IP Law; Gary M. Hartman; Domenica N. S. Hartman (57) ABSTRACT

Systems and methods suitable for decreasing catheter-associated bacteriuria in a catheterized patient include a urinary collection system having a collection bag, a drain tube fluidically connected to the collection bag to enable emptying urine collected in the collection bag, and a flexible continuous tube formed as an integral one-piece component and fluidically connected to the collection bag to enable urine to flow into the collection bag from a patient's bladder. Catheter-associated bacteriuria may be decreased in the system by instilling a sterile acetic acid solution into the collection bag via the continuous tube, dispersing the solution in the collection bag, draining the solution from the collection bag via the drain tube, and then allowing urine to flow from the catheterized patient through the continuous tube and into the collection bag.

17 Claims, 5 Drawing Sheets

(51) Int. Cl.
*A61B 5/00* (2006.01)
*A61B 5/145* (2006.01)

(52) U.S. Cl.
CPC ............ *A61F 5/442* (2013.01); *A61F 5/4404* (2013.01); *A61F 5/4405* (2013.01)

(56) References Cited

U.S. PATENT DOCUMENTS

| | | | | |
|---|---|---|---|---|
| 4,533,354 A | * | 8/1985 | Jensen | A61F 5/4405 383/44 |
| 4,564,361 A | | 1/1986 | Akiyama | |
| 4,704,102 A | | 11/1987 | Guthery | |
| 5,643,236 A | * | 7/1997 | Hadley | A61F 5/4408 128/DIG. 15 |
| 7,476,220 B2 | * | 1/2009 | Lillegaard | A61F 5/4404 4/144.2 |
| 8,361,044 B2 | | 1/2013 | Marshall | |
| 2003/0158540 A1 | * | 8/2003 | Washington | A61F 5/441 604/544 |
| 2005/0236329 A1 | * | 10/2005 | Brotherton | A61M 1/3489 210/645 |
| 2008/0294069 A1 | * | 11/2008 | Stickler | A61B 5/14539 600/584 |
| 2011/0251572 A1 | | 10/2011 | Nishtala et al. | |
| 2012/0184944 A1 | * | 7/2012 | Tomes | A61F 5/44 604/544 |
| 2013/0030262 A1 | * | 1/2013 | Burnett | A61B 5/0215 600/309 |
| 2017/0042723 A1 | * | 2/2017 | Oberholtzer | A61F 5/441 |

FOREIGN PATENT DOCUMENTS

| | | | | |
|---|---|---|---|---|
| GB | 2153231 A | * | 8/1985 | ............. A61F 5/44 |
| GB | 2215211 A | * | 9/1989 | ............. A61F 5/44 |
| JP | 2001314299 A | * | 11/2001 | ............. A61F 5/44 |

OTHER PUBLICATIONS

Supplemental Partial Search Report, dated Apr. 17, 2019, for European Patent Application No. 16 847515.0 (PCT/US2016/052388; 12 pages.

* cited by examiner

URINARY COLLECTION SYSTEM AND PROCEDURE FOR DECREASING CATHETER-ASSOCIATED BACTERIURIA

CROSS REFERENCE TO RELATED APPLICATIONS

This application claims the benefit of U.S. Provisional Application No. 62/220,316, filed Sep. 18, 2015, the contents of which are incorporated herein by reference. In addition, this application is related to U.S. Pat. No. 6,858,021, the contents of which are incorporated herein by reference.

BACKGROUND OF THE INVENTION

The present invention generally relates to equipment and techniques for reducing the incidence of infections in patients. The invention particularly relates to a urinary collection system suitable for use in reducing the incidence of urinary tract infections in patients with indwelling catheters.

Research data suggest that indwelling urethral catheters are the management techniques of choice for intractable urinary incontinence or chronic bladder outlet obstruction. The literature indicates that persistent, irreversible urinary incontinence may affect an estimated 50% of patients in tertiary care settings. However, patients who have an indwelling urinary catheter show a high incidence of urinary tract infections as demonstrated by numerous research studies. The catheterized urinary tract has been demonstrated to account for most nosocomial urinary tract infections with resulting bacteriuria. Complications of bacteriuria include obstructed catheters, acute pyelonephritis, bacteremia, periurethral purulent infections, vesicourethral reflux, chronic tubulointerstitial nephritis, chronic renal failure, and death. In addition, systemic symptoms of bacteriuria include fever above 38.4° C., nausea, vomiting, and costovertebral angle tenderness, as well as catheter-related hypovolemic sepsis. The literature supports nontreatment for asymptomatic bacteriuria. Long-term urethral catheterization has been linked with symptomatic bacteriuria (e.g., fever, costovertebral angle, or suprapubic tenderness). Notwithstanding, long-term urethral catheter-associated bacteriuria is said to be the most common nosocomial infection in secondary and tertiary care settings, as well as in home health care environments.

Research studies have indicated that about 40% of all nosocomial infections in the United States are associated with the urinary tract, of which 75% are related directly to indwelling catheterization. Bacteriuria has been demonstrated as a universal consequence of long-term urethral catheterization, where the majority of urinary tract infections occur through microbial ascension from the distal urethral tubule into the bladder cavity. The bladder normally resists infection by two known mechanisms: (1) mechanical factors (i.e., residual urine and the bladder urine volume) and (2) intrinsic factors (i.e., the antibacterial property of the bladder mucosa, urea concentration, osmolarity, and pH, as well as antimicrobial drugs). Factors that contribute to urinary tract infections include structural defects, systemic disorders, sexually transmitted diseases, insertion of a urethral catheter, and long-term indwelling catheterization. Urethral catheterization obliterates the natural cleansing of the urinary mucosa, encouraging the migration of pathogens into the bladder.

Antibiotic-resistant microorganisms are prevalent in long-term care facilities, and long-term indwelling catheters are convenient for transmission of antibiotic-resistant bacterial flora such as (in descending order of frequency) *Providencia stuartii, Proteus mirabilis, Morganella morganii,* Group D *Streptococcus, Staphylococcus aureus, Pseudomonas aeruginosa, Escherichia coli, Klebsiella pneumoniae, Entrococcus,* and *Entrobacter.* Moreover, research studies have found that antiseptic bladder irrigation did not prevent bacteriuria in patients with long-term catheters but, rather, promoted antibiotic-resistant microorganisms. Accordingly, routine antiseptic bladder irrigation was not recommended for patients with long-term indwelling catheters. Instead, patient education with regard to long-term catheterization has been recommended as an effective measure in reducing the incidence of catheter-related bacteriuria. However, education of patients by medical personnel appears to be inconsistent and not comprehensive, especially in the case of the elderly.

In summary, the use of an indwelling catheter has been frequently associated with acute bacteriuria, regardless of strict adherence to urinary catheter care guidelines, and though the use of antibiotic bladder irrigation has been found to reduce the incidence of infection, it has also been shown to lead to the emergence of resistant organisms. As a solution, U.S. Pat. No. 6,858,021 to Washington provides a method for reducing the incidence of urinary tract infection in patients having indwelling catheters through the use of a weak acidic solution to treat the catheter collection bag used by the patient. The method decreases catheter-associated bacteriuria in a catheterized patient by instilling a sterile acetic acid solution (e.g., distilled vinegar) into the catheter collection bag, dispersing the solution in the bag, and then draining the solution from the bag. Thereafter, urine is allowed to flow from the catheterized patient through a catheter and into the bag.

While the teachings of Washington are able to substantially reduce both the type and number of colony-forming bacteria in a catheter drainage receptacle, and such a capability is particularly beneficial to patients with long-term indwelling urethral catheters by decreasing a patient's risk in polymicrobial bacterial propagation within the catheter drainage system, further advancements in such treatments are continuously desired.

BRIEF DESCRIPTION OF THE INVENTION

The present invention provides systems and methods suitable for decreasing catheter-associated bacteriuria in a catheterized patient.

According to one aspect of the invention, a urinary collection system is provided that includes a collection bag having an interior equipped with means for creating a hinge at which the collection bag is able to bend, a drain tube fluidically connected to the collection bag to enable emptying urine collected in the collection bag, a flexible continuous tube fluidically connected to the collection bag to enable urine to flow into the collection bag from a patient's bladder wherein the continuous tube is an integral one-piece component, an irrigation port on the continuous tube for instilling an irrigation solution at the drainage tube portion, a urine collection port on the continuous tube for withdrawing urine from the continuous tube, one or more turn valves on the continuous tube to prevent reflux of the irrigation solution into the patient's bladder, means for performing one or more chemical measurements of urine flowing through the continuous tube, diagnostic means interfacing with the chemical measurement means to quantitatively and/or qualitatively analyze the one or more chemical measurements of the urine, and one or more connectors that enable the collection bag to be mounted to a surface.

According to another aspect of the invention, a method of using a urinary collection system to decrease catheter-associated bacteriuria in a catheterized patient is provided. The urinary collection system includes a collection bag, a drain tube fluidically connected to the collection bag to enable emptying urine collected in the collection bag, and a flexible continuous tube formed as an integral one-piece component and fluidically connected to the collection bag to enable urine to flow into the collection bag from a patient's bladder. The method includes instilling a sterile acetic acid solution into the collection bag via the continuous tube, dispersing the solution in the collection bag, draining the solution from the collection bag via the drain tube, and then allowing urine to flow from the catheterized patient through the continuous tube and into the collection bag.

Technical effects of the system and method described above preferably include the ability to decrease catheter-associated bacteriuria in a catheterized patient by reducing the number of extraneous sources of contamination and infection, as well as performing and quantitatively and/or qualitatively analyzing one or more chemical measurements directly on the urine within the system.

Other aspects and advantages of this invention will be further appreciated from the following detailed description.

DETAILED DESCRIPTION OF THE INVENTION

In part, the present invention was prompted by research reported in U.S. Pat. No. 6,858,021 to Washington, which evidenced that the instillation of a weak acidic irrigation solution into a urinary collection system is capable of significantly reducing the type and number of certain kinds of microorganisms in urinary collection systems that use catheter collection bags, thereby reducing the incidence of urinary tract infections in patients having indwelling catheters. The present invention offers additional features for urinary collection systems that enable periodic catheter irrigation. A nonlimiting embodiment of such a urinary collection system 10 shown in FIG. 1 and nonlimiting embodiments of collection bags (receptacles) 12 and 112 shown in FIG. 1 through 3 allow for the convenient instillation of an irrigation solution (preferably a sterile acetic acid solution, e.g., distilled acetic vinegar, or other antimicrobial agent), as well as decreased cross-contamination during changing of the collection receptacle (bag). To facilitate the description provided below of the embodiments represented in the drawings, relative terms, including but not limited to, "vertical," "horizontal," "lateral," "front," "rear," "side," "forward," "rearward," "upper," "lower," "above," "below," "right," "left," etc., may be used in reference to the orientations of the collection bags 12 and 112 during their use by a patient as represented in the drawings, and therefore are relative terms that indicate the construction and use of the invention and therefore help to define the scope of the invention.

Figure 1:
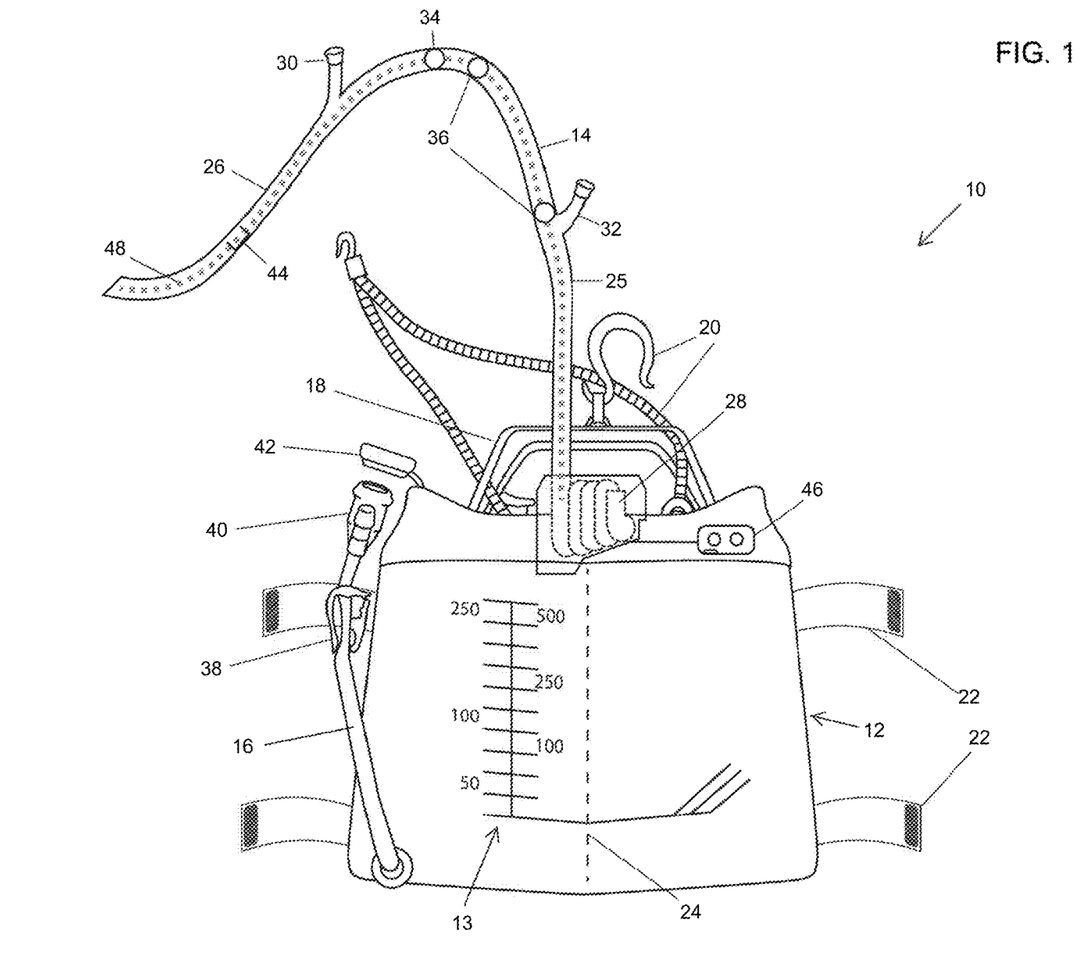
FIG. 1 is a nonlimiting schematic representation of a urinary collection system suitable for use in the present invention.

The nonlimiting embodiment of the urinary collection system 10 schematically represented in the FIG. 1 shows the collection bag 12 thereof equipped with a continuous tube 14 through which urine flows into the bag 12 from the bladder of an individual (hereinafter, "patient"), and a drain tube 16 for emptying urine collected in the bag 12. The continuous tube 14 is preferably formed of a soft, flexible and antimicrobial material of any suitable type known in the art. The drain tube 16 is not required to be antimicrobial, and may be formed of a soft and flexible material such as rubber, polyurethane, silicone, etc. The collection bag 12 may be made of a soft antimicrobial vinyl and preferably has a capacity sufficient for the intended patient. A removable handle 18 is shown as being provided for carrying the bag 12. The system 10 is further equipped with one or more connectors 20 that permit the collection bag 12 to be mounted to a fixed surface, such as a bed, in any suitable manner, or secured to the patient, for example, to the patient's leg in any suitable manner. For purposes of the latter, the bag 12 is represented as being equipped with leg straps 22 by which the bag 12 can be secured around a patient's leg. The interior of the bag 12 is equipped with a "zip-lock" or other reversible separator 24 that facilitates placement of the bag 12 around the leg by creating a vertical hinge at which the bag 12 is able to bend at or near its midsection. The bag 12 may include markings 13 thereon, for example, for use in measuring a volume of urine contained in the bag 12.

The continuous tube 14 generally comprises a portion identified as a drainage tube 25 and a portion identified as a Foley catheter 26, though other types of indwelling urinary catheters are also within the scope of the invention. The drainage tube 25 is disposed between the catheter 26 and the collection bag 12. The continuous tube 14 is represented as further comprising a portion identified as an extendable/retractable tubing 28 disposed between the drainage tube 25 and the collection bag 12 that enables the continuous tube 14 to be extended or retracted as may be desired for the convenience or comfort of the patient. The continuous tube 14 is preferably an integrally-formed one-piece component. The lack of any separation between the catheter 26, drainage tube 25, and extendable/retractable tubing 28 reduces the number of extraneous sources of contamination and infection within the system 10.

The continuous tube 14 is also represented as comprising various ports, in particular, an inflation port 30 that can be used to inflate a balloon (not shown) commonly associated with Foley catheters, and an irrigation port 32 for instilling the irrigation solution at the drainage tube 25 of the continuous tube 14. A urine collection port 34 is provided that permits the withdrawal of urine from the continuous tube 14 (as well as instillation of fluids), and one or more turn valves 36 are provided that may be used to prevent reflux of the irrigation solution into the patient's bladder, perform diagnostic investigations, and/or use for other purposes that may entail fluidically isolating the catheter 26 from the drainage tube 25 and/or collection bag 12.

The drain tube 16 includes a one-way turn valve 38 (or other suitable closure), a retractable drain spigot bell 40, and a cap 42. The drain spigot bell 40 preferably includes a viscus chlorine gel to inhibit bacterial growth when emptying the bag 12, and the turn valve 38 prevents back flow of urine into the bag 12.

The catheter portion 26 of the continuous tube 14 preferably includes a sensing device in the form of a urine analyzer 44 adapted to perform one or more chemical measurements on urine as it flows through the continuous tube 14. The urine analyzer 44 is preferably hypo-allergic, nonhazardous to humans, and resistant to deterioration and biodegradation within the bio-environment in which it operates. Such a urine analyzer 44 may be a microfluidic system fabricated on a silicon semiconductor chip and specifically adapted for biomedical analysis, commonly referred to as a laboratory on a chip (lab-on-a-chip). A nonlimiting example of such a device is disclosed in a paper published online and entitled "A Lab-on-a-Chip for Biological Fluids Analysis," incorporated herein by reference and available from Graca Minas through the ResearchGate website, www.researchgate.net. The urine analyzer 44 is preferably configured to measure and/or detect levels of one or more of nitrates, urobilinogen, proteins, glucose, pH, hemoglobin, blood, volume, specific gravity, ketones, bilirubin, bacteria, and yeast.

The urine analyzer 44 preferably interfaces with a diagnostic unit 46 that performs quantitative and/or qualitative analysis of the data relating to the composition of the urine sensed with the urine analyzer 44. The urine analyzer 44 may wirelessly communicate with the diagnostic unit 46, allowing the diagnostic unit 46 to be located anywhere on the collection bag (for example, as shown in FIG. 1), or remotely located from the collection bag. For this purpose, FIG. 1 schematically represents the catheter 26 as incorporating a conductor 48 that serves as an antenna for wirelessly transmitting data from the urine analyzer 44 to the diagnostic unit 46. In some embodiments, the function of the antenna can be performed with a radiopaque strip of a type commonly provided in catheters to promote their visibility under X-ray examination, in which case the radiopaque strip may be formed of or contain an electrically-conductive radiocontrast material (nonlimiting examples include titanium and tungsten) and is electrically connected to the output of the urine analyzer 44.

The diagnostic unit 46 may include any components suitable for communicating with the urine analyzer 44 and performing the desired analysis, including but not limited to a microprocessor, solid-state memory, and a replaceable and/or rechargeable battery. The diagnostic unit 46 may include a visual indicator, screen, or other means for communicating results of the quantitative and/or qualitative analysis of the data relating to the composition of the urine, as well as push-buttons or the like for direct user interfacing. As a nonlimiting example, the diagnostic unit 46 may be configured to enable the patient to wirelessly access the results of the quantitative and/or qualitative analysis from a personal computer, website, mobile phone, or other means. Measurements performed on the urine and the quantitative and/or qualitative analysis thereof may be performed on demand, periodically, or continuously in order to monitor the health of the patient. The urine collection port 34 can be used to withdraw urine for the purpose of verifying results obtained with the urine analyzer 44.

Figure 2:
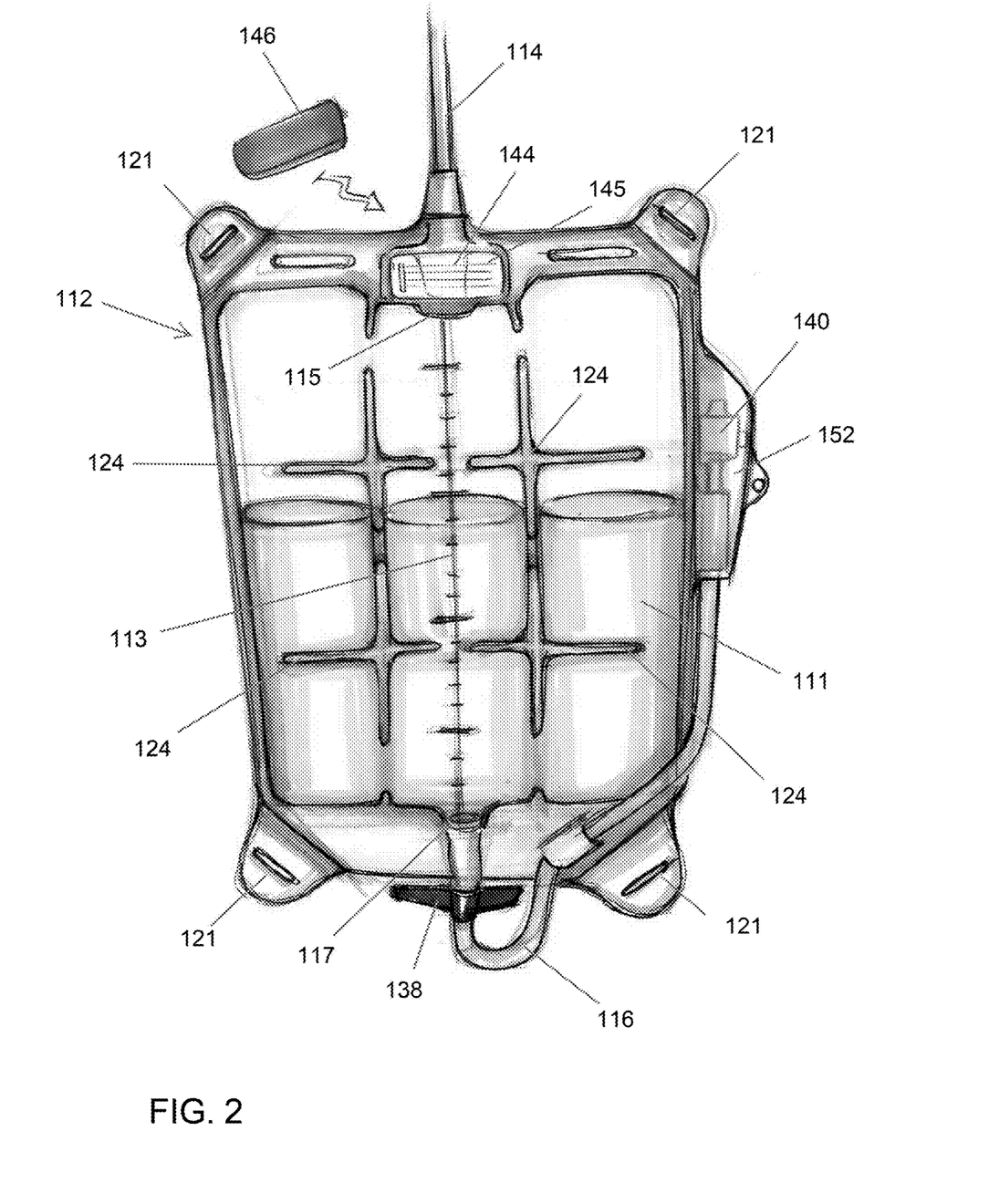
FIG. 2 schematically represents a second nonlimiting embodiment of a collection bag suitable for use with the urinary collection system of FIG. 1.
Figure 3:
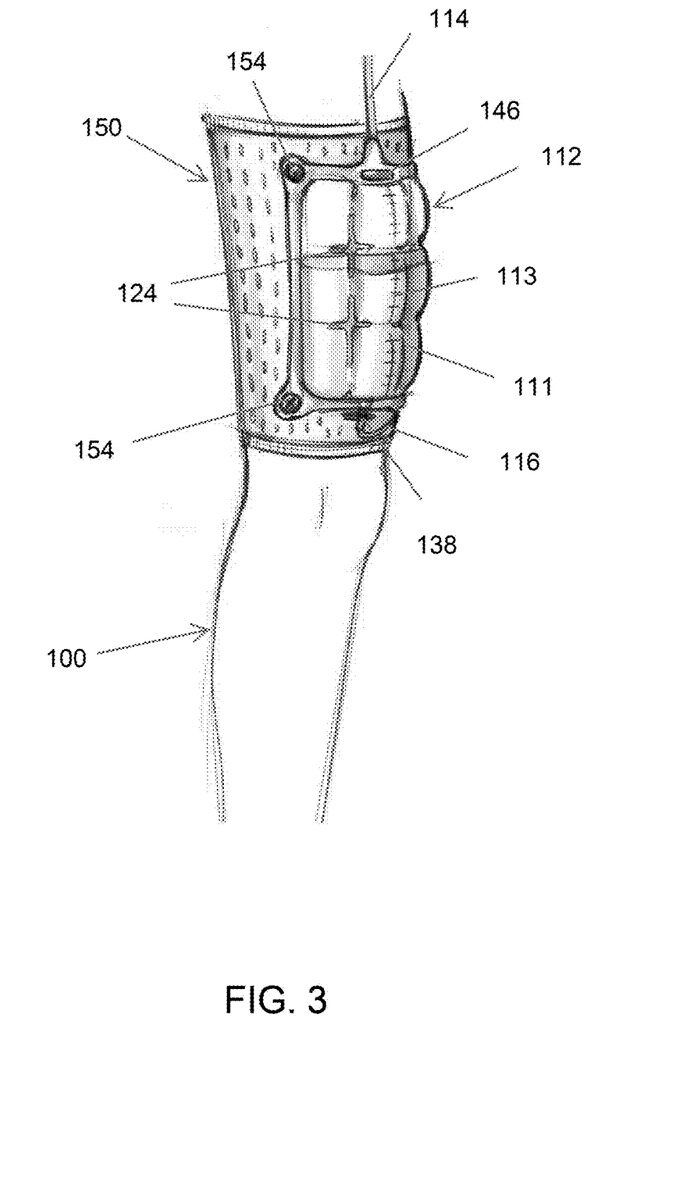
FIG. 3 schematically represents the collection bag of FIG. 2 secured to a patient's leg with a sleeve in accordance with a nonlimiting aspect of the invention.

FIGS. 2 and 3 represent the collection bag 112 and components thereof as another embodiment suitable for use in place of the bag 12 represented in the system 10 of FIG. 1. In FIGS. 2 and 3, consistent reference numbers are used to identify the same or functionally equivalent elements, but with a numerical prefix (1, 2, or 3, etc.) added to distinguish the particular embodiment from the embodiment of FIG. 1. Other aspects of the bag 112 and its interaction with other components of the system 10 not discussed in any detail can be, in terms of structure, function, materials, etc., essentially as was described for the first embodiment.

FIG. 2 schematically represents the collection bag 112 as having an inlet 115 connected to a continuous tube 114 through which urine flows from the bladder of a patient and collects in the bag 112. FIG. 2 also schematically represents a drain tube 116 connected to an outlet 117 of the bag 112 for emptying urine 111 that has been collected in the bag 112. The continuous tube 114 may include some or all of the features discussed in regards to the continuous tube 14 of FIG. 1. Similar to the drain tube 16 of FIG. 1, the drain tube 116 preferably includes a one-way turn valve 138 (or other suitable closure) and a drain spigot 140. While not in use, the drain spigot 140 may be removably stowed in an antibacterial pocket 152.

The interior of the bag 112 is equipped with multiple separators 124 along which the bag 112 is able to bend. The separators 124 effectively form pivot joints or hinges of the bag 112, and may be arranged in a grid such that bending of the bag 112 is promoted in multiple directions at multiple locations. For example, in the embodiment represented in FIG. 2, the separators 24 of the bag 112 define a grid that enables the bag 112 to bend along two vertical hinges and two horizontal hinges (relative to the orientation in FIG. 2) and effectively create nine fluidically connected volumes or sections within the bag 112. The bag 112 may include markings 113 thereon, for example, for use in measuring the volume of urine 111 contained in the bag 112.

The bag 112 includes a sensing device in the form of a urine analyzer 144 adapted to perform one or more chemical measurements on urine as it flows through the continuous tube 114 and into the bag 114. As such, the urine analyzer 144 is represented as being located at the inlet 115 or directly above the inlet 115, and in-line with the flow of the incoming urine from the continuous tube 114. The urine analyzer 144 may be functionally equivalent to the urine analyzer 44 of FIG. 1, and may interface, either directly or wirelessly, with a diagnostic unit 146 that performs quantitative and/or qualitative analysis of the data relating to the composition of the urine sensed with the urine analyzer 144. According to one nonlimiting aspect of the bag 112, as represented in FIG. 2, the urine analyzer 144 may be built into the bag 112 and disposable therewith, whereas the diagnostic unit 146 may be removed prior to disposal of the bag 112. For example, FIG. 2 represents the diagnostic unit 146 as being configured to functionally couple to the urine analyzer 144 via electrodes 145 located on the bag 112.

The bag 112 is represented as being equipped with tabs 121 by which the bag 112 can be secured to a fixed surface in any suitable manner, or secured to a patient, for example, to the patient's leg in any suitable manner. For example, FIG. 2 represents the tabs 121 as including slots formed therein that are configured to accept fastening devices for securing the bag 112 to another object. As a nonlimiting example, FIG. 3 represents the slots as accepting fasteners 154 for removably securing the bag 112 to a sleeve 150 worn on a patient's leg 100. In this nonlimiting embodiment, the fasteners 154 (represented as buttons) are located on the sleeve 150 and inserted into the slots of the tabs 121, which are located at four corners of the bag 112 in order to hold the bag 112 against the sleeve 150. As represented, the hinges in the bag 112 defined by the separators 124 promote the ability of the bag 112 to conform to the shape of the patient's leg 100, thereby promoting comfort and reducing the profile of the bag 112. The sleeve 150 may be formed of any material, preferably washable, moisture wicking, and/or breathable fabrics of the types commonly used for sporting or medical applications.

Figure 4:
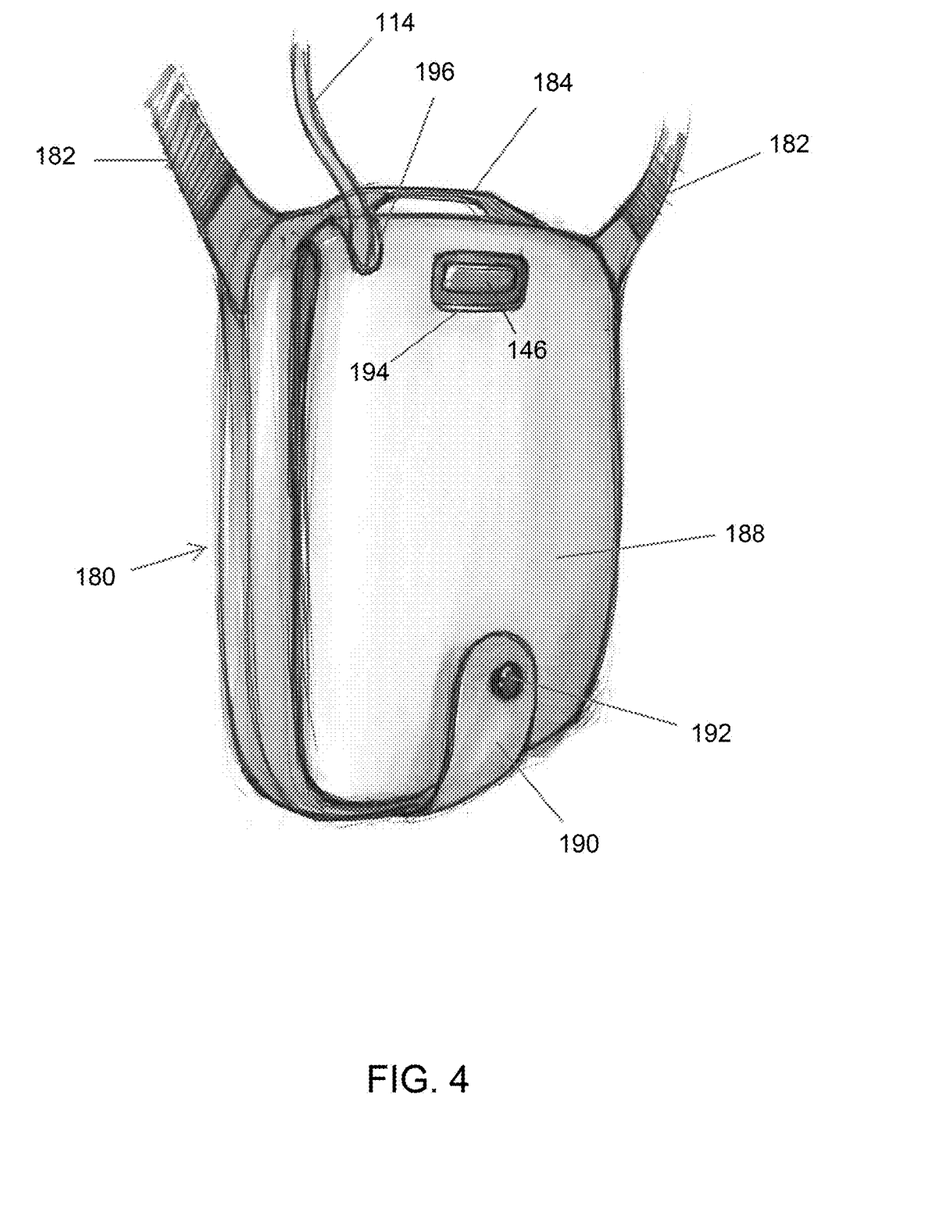
FIGS. 4 and 5 schematically represent a carrying case for use with the collection bag of FIG. 2 depicted in closed and open positions, respectively, in accordance with a nonlimiting aspect of the invention.
Figure 5:
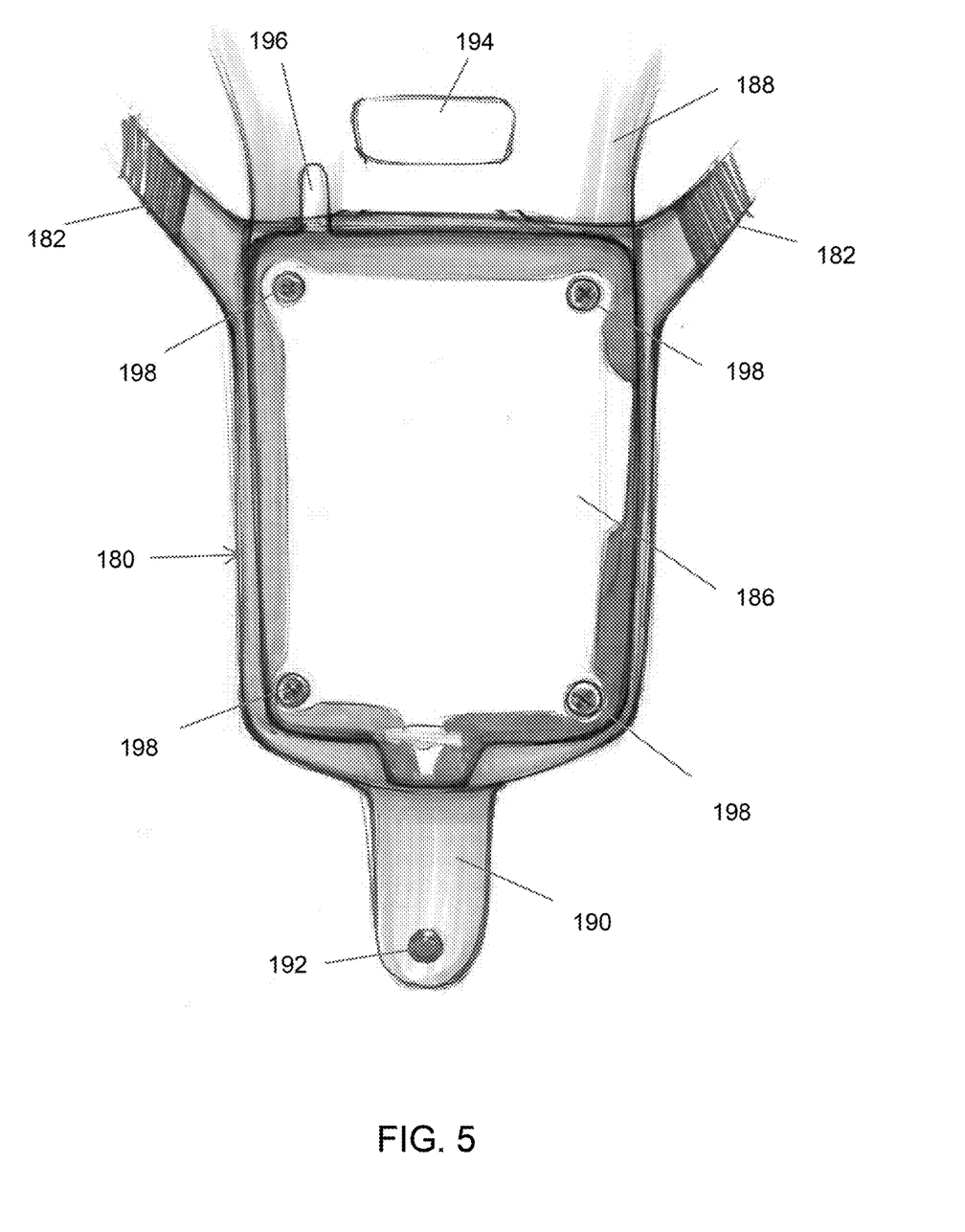

FIGS. 4 and 5 schematically represent a nonlimiting embodiment of a carrying case 180 configured to hold the bag 112 during transport. The case 180 has an interior cavity closable by a cover 188. An interior surface 186 of the cavity comprises protrusions 198 (FIG. 5) configured to be inserted into the slots in the tabs 121 of the bag 112 and thereby secure the bag 112 against the surface 186 within the case 180. The cover 188 may be used to conceal the bag 112 within the cavity during use of the case 180 as represented in FIG. 4, which further represents the cover 188 as being secured in a closed position with a flap 190 and fastener 192. The cover 188 is represented as including a hole 196 at its upper end to allow the continuous tube 114 to be routed from the interior cavity of the bag 112 to its exterior. In addition, a hole 194 is provided at the upper end of the cover 188 to provide access to the urine analyzer 144, for example, to visually observe a visual indicator (such as a light) or a display screen (not shown) on the analyzer 144. The case 180 may include straps 182 and/or a handle 184 in order to promote convenient transportation of the case 180 and the bag 112 stowed therein.

The urinary collection system 10 represented in the drawings has the potential for reducing catheter-associated urinary tract infections and the nosocomial spread of bacteria. In use, a sterile acetic acid solution can be installed into the collection bag 12 or 112 via the continuous tube 14 or 114, after which the solution can be dispersed in the collection bag 12 or 112 and then drained from the bag 12 or 112 via the drain tube 16 or 116. Afterwards, use of the system 10 by a catheterized patient can resume by allowing urine to flow from the patient through the continuous tube 14 or 114 and into the collection bag 12 or 112. To provide certain benefits believed to be associated with the use of the system 10, an effective amount of irrigation solution is generally that which will coat at least the entire interior of the collection bag 12 or 112. As such, the amount of solution necessary to reduce the incidence of bacterial growth and its subsequent propagation into the bladder will depend in part of the capacity of the bag 12 or 112. However, it is believed that a standard instillation dose of about thirty to about fifty milliliters is sufficient to lower bacterial colony counts below pathogenic levels, with the use of lower and higher doses being foreseeable. Using such solutions to reduce bacterial colony count within a collection bag, that is, decreasing a patient's risk in polymicrobial bacterial propagation within the urinary collection system 10, can reduce the incidence of catheter-acquired bladder bacteriuria.

While the invention has been described in terms of specific embodiments, it is apparent that other forms could be adopted by one skilled in the art. For example, the physical configuration of the system 10 or its components could differ from that shown, and materials and processes/methods other than those noted could be used. In addition, the invention encompasses additional embodiments in which one or more features or aspects of different disclosed embodiments may be combined. Therefore, the scope of the invention is to be limited only by the following claims.

The invention claimed is:

1. A urinary collection system comprising:
   a collection bag having an interior equipped with vertical internal hinges and horizontal internal hinges at which the collection bag bends vertically and horizontally, wherein each vertical internal hinge is created by multiple vertical separators within the interior of the collection bag that are aligned so that each vertical internal hinge extends across a majority of a vertical length of the interior, wherein each horizontal hinge is created by multiple horizontal separators within the interior of the collection bag that are aligned so that each horizontal internal hinge extends across a majority of a horizontal width of the interior, each respective vertical separator intersects a respective horizontal separator such that multiple cross-shaped intersections joining opposing outer walls of the collection bag are defined so as to create fluidically connected volumes within the collection bag;
   a drain tube fluidically connected to the collection bag to enable emptying urine collected in the collection bag;
   a flexible continuous tube fluidically connected to the collection bag to enable the urine to flow into the collection bag from a bladder of a catheterized patient, the continuous tube being an integral one-piece component;
   an irrigation port on the continuous tube for instilling an irrigation solution in the continuous tube;
   a urine collection port on the continuous tube for withdrawing the urine from the continuous tube;
   one or more turn valves on the continuous tube to prevent reflux of the irrigation solution into the bladder of the catheterized patient;
   a urine analyzer for performing one or more chemical measurements of the urine flowing through the continuous tube; and
   diagnostic means interfacing with the urine analyzer to quantitatively and/or qualitatively analyze the one or more chemical measurements of the urine.

2. The urinary collection system of claim 1, wherein the continuous tube comprises a catheter portion, an extendable/retractable tubing that fluidically connects the continuous tube to the collection bag, and a drainage tube portion therebetween, the continuous tube lacking any separation between the catheter portion, the drainage tube, and the extendable/retractable tubing to reduce extraneous sources of contamination and infection within the system.

3. The urinary collection system of claim 1, wherein the urine analyzer is located on the continuous tube.

4. The urinary collection system of claim 1, wherein the urine analyzer is located at or adjacent to an inlet of the collection bag and inline with the continuous tube.

5. The urinary collection system of claim 1, further comprising one or more connectors on the collection bag that enable the collection bag to be secured to a surface.

6. The urinary collection system of claim 1, further comprising one or more connectors on the collection bag that are configured to mount the collection bag to a bed or a leg of the catheterized patient.

7. The urinary collection system of claim 1, wherein the drain tube comprises a closure, a retractable drain spigot bell, and a cap.

8. The urinary collection system of claim 7, wherein the drain spigot bell includes a viscous chlorine gel to inhibit bacterial growth when emptying the collection bag through the drain tube.

9. The urinary collection system of claim 1, wherein the collection bag includes a pocket configured to store at least an end of the drain tube and to inhibit bacterial growth.

10. The urinary collection system of claim 1, wherein the multiple vertical and horizontal separators are reversible separators.

11. The urinary collection system of claim 1, further comprising a sleeve configured to be worn on a leg of the catheterized patient and having fasteners thereon for securing the collection bag.

12. The urinary collection system of claim 1, further comprising a hanging bracket having fasteners thereon for supporting the collection bag and configured to be hung from a bed.

13. The urinary collection system of claim 1, further comprising a carrying case having fasteners thereon for supporting and securing the collection bag to the carrying case, and a cover for concealing at least a portion of the collection bag within the carrying case.

14. A method of using the urinary collection system of claim 1 to decrease catheter-associated bacteriuria in the catheterized patient, the method comprising:
   instilling a sterile acetic acid solution as the irrigation solution into the irrigation port, through the continuous tube, and into the collection bag;
   dispersing the sterile acetic acid solution in the collection bag;
   draining the sterile acetic acid solution from the collection bag; and then
   allowing the urine to flow from the catheterized patient through the continuous tube and into the collection bag.

15. The urinary collection system of claim 1, further comprising a radiopaque strip on the continuous tube, where the radiopaque strip is electrically connected to the urine analyzer and serves as an antenna for wirelessly transmitting the one or more chemical measurements from the urine analyzer to the diagnostic means.

16. The urinary collection system of claim 1, wherein the multiple vertical and horizontal separators within the interior of the collection bag create a grid of the fluidically-connected volumes within the collection bag.

17. A urinary collection system comprising:
   a collection bag having an interior equipped with vertical internal hinges and horizontal internal hinges at which the collection bag bends vertically and horizontally, wherein each vertical internal hinge is created by multiple vertical separators within the interior of the collection bag that are aligned so that each vertical internal hinge extends across a majority of a vertical length of the interior, wherein each horizontal hinge is created by multiple horizontal separators within the interior of the collection bag that are aligned so that each horizontal internal hinge extends across a majority of a horizontal width of the interior, each respective vertical separator intersects a respective horizontal separator such that multiple cross-shaped intersections joining opposing outer walls of the collection bag are defined so as to create fluidically connected volumes within the collection bag;

a drain tube fluidically connected to the collection bag to enable emptying urine collected in the collection bag;

a flexible continuous tube fluidically connected to the collection bag to enable the urine to flow into the collection bag from a bladder of a catheterized patient, the continuous tube being an integral one-piece component comprising a catheter portion and a drainage tube portion connecting the catheter portion to the collection bag, the continuous tube lacking any separation between the catheter portion and the drainage tube to reduce extraneous sources of contamination and infection within the system;

a radiopaque strip on the flexible continuous tube;

an irrigation port on the continuous tube for instilling an irrigation solution in the continuous tube;

a urine collection port on the continuous tube for withdrawing the urine from the continuous tube; and a urine analyzer on the continuous tube for performing one or more chemical measurements on the urine as the urine is flowing through the continuous tube, the urine analyzer being electrically connected to the radiopaque strip which serves as an antenna for wirelessly transmitting the one or more chemical measurements from the urine analyzer to a diagnostic unit that performs quantitative and/or qualitative analysis of the one or more chemical measurements performed by the urine analyzer.

* * * * *